(12) United States Patent
Liang et al.

(10) Patent No.: US 10,336,682 B1
(45) Date of Patent: Jul. 2, 2019

(54) HYDROXYTYROSOL SHIKIMIC ACID ESTER FOR TREATING CARDIOVASCULAR DECEASES AND A METHOD OF PREPARING THE SAME

(71) Applicants: Chengyuan Liang, Xi'an (CN); Lei Tian, Xi'an (CN); Yuzhi Liu, Xi'an (CN); Xingke Ju, Xi'an (CN); Nan Hui, Xi'an (CN); Mi Wu, Xi'an (CN); Juan Li, Xi'an (CN); Han Li, Xi'an (CN); Bin Tian, Xi'an (CN); Qianqian Zhao, Xi'an (CN); Gennian Mao, Xi'an (CN); Nan Qin, Xi'an (CN); Juan Xia, Xi'an (CN); Zhenfeng Shi, Xi'an (CN)

(72) Inventors: Chengyuan Liang, Xi'an (CN); Lei Tian, Xi'an (CN); Yuzhi Liu, Xi'an (CN); Xingke Ju, Xi'an (CN); Nan Hui, Xi'an (CN); Mi Wu, Xi'an (CN); Juan Li, Xi'an (CN); Han Li, Xi'an (CN); Bin Tian, Xi'an (CN); Qianqian Zhao, Xi'an (CN); Gennian Mao, Xi'an (CN); Nan Qin, Xi'an (CN); Juan Xia, Xi'an (CN); Zhenfeng Shi, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/359,982

(22) Filed: Mar. 20, 2019

(30) Foreign Application Priority Data

Mar. 1, 2019 (CN) .......................... 2019 1 0153094

(51) Int. Cl.
*C07C 69/757* (2006.01)
*B01J 31/02* (2006.01)
*C07C 67/08* (2006.01)

(52) U.S. Cl.
CPC ......... *C07C 69/757* (2013.01); *B01J 31/0244* (2013.01); *C07C 67/08* (2013.01); *C07C 2601/16* (2017.05)

(58) Field of Classification Search
CPC ... C07C 69/757; C07C 67/08; C07C 2601/16; B01J 31/0244
See application file for complete search history.

(56) References Cited

PUBLICATIONS

Appendino et al., chemoselective esterification of phenolic acids and alcohols (Organic Letters vol. 4, No. 22, 2002, pp. 3839-3841).*

* cited by examiner

Primary Examiner — Jafar F Parsa

(57) ABSTRACT

A compound having the following formula I:

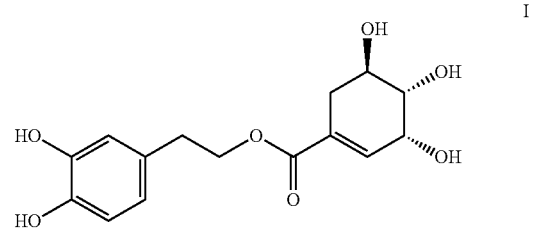

is disclosed. A method of preparing the compound of formula I is also disclosed.

12 Claims, 2 Drawing Sheets

HYDROXYTYROSOL SHIKIMIC ACID ESTER FOR TREATING CARDIOVASCULAR DECEASES AND A METHOD OF PREPARING THE SAME

The present invention claims priority to Chinese Patent Application No.: 201910153094.9, filed on Mar. 1, 2019, which is incorporated by reference for all purposes as if fully set forth herein.

FIELD OF THE INVENTION

The present invention relates to pharmaceuticals, in particular, to a hydroxytyrosol shikimic acid ester for treating cardiovascular diseases and a method of preparing the same.

BACKGROUND OF THE INVENTION

As the population ages, cardiovascular diseases have surpassed cancer as number one threat to human health. Hypertension, insulin resistance, dyslipidemia, and arteriosclerosis are risk factors for cardiovascular diseases, and their damages to target organs have been confirmed by large-scale epidemiological investigations. A large number of studies have found that the reduction of the body's antioxidant capacity, oxidation and anti-oxidation imbalance, and excessive production of reactive oxygen species (ROS) play an important role in the occurrence of cardiovascular diseases.

Hydroxytyrosol (4-(2-hydroxyethyl)-1,2-benzenediol; compound of formula II) (CAS:10597-60-1) is a phenylethanoid, a type of phenolic phytochemical with antioxidant properties in vitro. In nature, hydroxytyrosol is found in olive leaf and olive oil, in the form of its elenolic acid ester oleuropein and, especially after degradation, in its plain form.

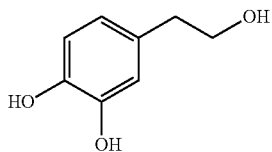

II

Shikimic acid ((3R,4S,5R)-3,4,5-Trihydroxycyclohex-1-enecarboxylic acid; compound of formula III) (CAS: 138-59-0) is present in the dried ripe fruit of the Magnoliaceae. Shikimic acid has anti-inflammatory and analgesic effects by affecting arachidonic acid metabolism, inhibiting platelet aggregation, arterial and venous thrombosis, and cerebral thrombosis, and can be used as an intermediate for antiviral and anticancer drugs.

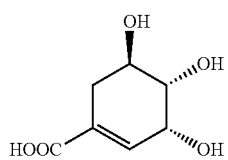

III

SUMMARY OF THE INVENTION

In one embodiment, the present invention provides a compound having the following formula I:

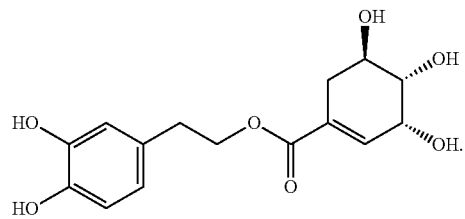

I

In another embodiment, the present invention provides a method of preparing the compound of formula I. The method includes: reacting the compound of formula II with the compound of formula III to obtain the compound of formula I:

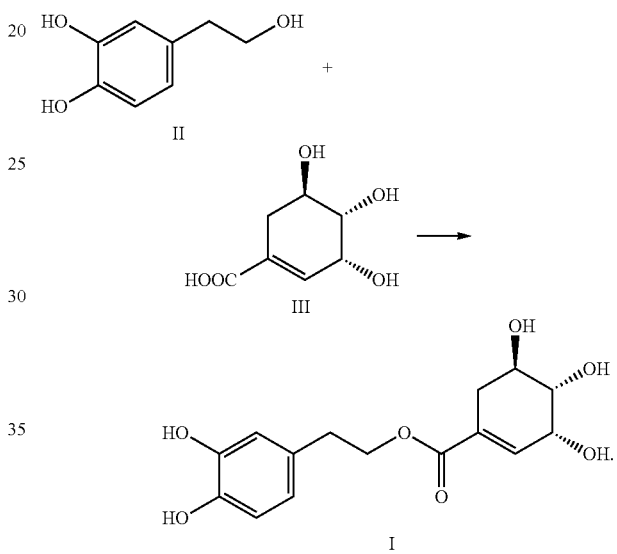

In another embodiment, the reaction of the compound of formula II with the compound of formula III includes the following steps: dissolving the compound of formula II and the compound of formula III in an organic solvent to form a reaction mixture under nitrogen atmosphere; adding a catalyst and a dehydrating agent to the reaction mixture; and heating the reaction mixture at 40-50° C. for 8-10 hours under sonication.

In another embodiment, the organic solvent is acetonitrile, THF, or DMF.

In another embodiment, the organic solvent is preferably acetonitrile.

In another embodiment, the molar ratio of the compound of formula II and the compound of formula III is 1:1 to 1.5:1.

In another embodiment, the molar ratio of the compound of formula II and the compound of formula III is preferably 1.2:1.

In another embodiment, the dehydrating agent is DCC, concentrated sulfuric acid, or EDC.

In another embodiment, the dehydrating agent is preferably DCC.

In another embodiment, the catalyst is DMAP.

In another embodiment, the reaction mixture is heated at 45° C.

In another embodiment, the reaction mixture is heated for 4 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

The inventors synthesized a novel hydroxytyrosol shikimic acid ester (formula I) by esterification of hydroxytyrosol and shikimic acid. It is expected that the new compound has higher efficacy in the treatment of cardiovascular diseases than the hydroxytyrosol or shikimic acid alone, and it can be used as a novel cardiovascular drug. In addition, hydroxytyrosol is instable in vivo and in vitro. Researcher are working on structural modification to improve stability. Accordingly, the present invention provides a synthetic route using hydroxytyrosol and shikimic acid as starting materials to synthesize the hydroxytyrosol shikimic acid ester. The reaction is simple and safe. The yield is high, and it is suitable for industrial production. The hydroxytyrosol shikimic acid ester better anticoagulant effects than hydroxytyrosol and shikimic acid in pharmacological tests.

Example 1

Preparation of the Hydroxytyrosol Shikimic Acid Ester 50 mg (0.32 mmol) of hydroxytyrosol and 47 mg (0.27 mmol) of shikimic acid were placed in a 100 mL reactor. 50 mL of acetonitrile was added to dissolve hydroxytyrosol and shikimic acid. 55.7 mg (0.27 mmol) of DCC (N,N'-Dicyclohexylcarbodiimide) and 0.4 mg DMAP (4-Dimethylaminopyridine) were added to the reaction mixture under nitrogen atmosphere. The reaction mixture was heated at 45° C. under sonication for 4 hours. The mixture was then cooled to room temperature, and concentrated under reduced pressure. 50 mL ethyl acetate and 100 mL water were then added to the mixture, and the organic phase was collected and concentrated to give a crude product. The crude product was purified by flash chromatography to obtain 74.3 mg of target product, a yield of 88.7%.

Hydroxytyrosol shikimic acid ester: $^1$H-NMR (300 MHz, DMSO-$d_6$) δ (ppm): 8.85 (2H, s), 7.55~7.22 (3H, m), 6.78 (1H, s), 5.93 (1H, s), 5.32 (1H, d), 4.71~4.47 (3H, m), 2.85 (3H, m), 2.17 (2H, m), 1.85-1.40 (2H, m); $^{13}$C-NMR (75 MHz, DMSO-$d_6$) δ (ppm): 166.46, 149.59, 144.55, 136.91, 130.56, 127.32, 122.44, 116.37, 114.71, 70.25, 67.69, 64.53, 35.37, 31.46; MS (ESI) for (M+H)$^+$: 311.5.

Figure 1:
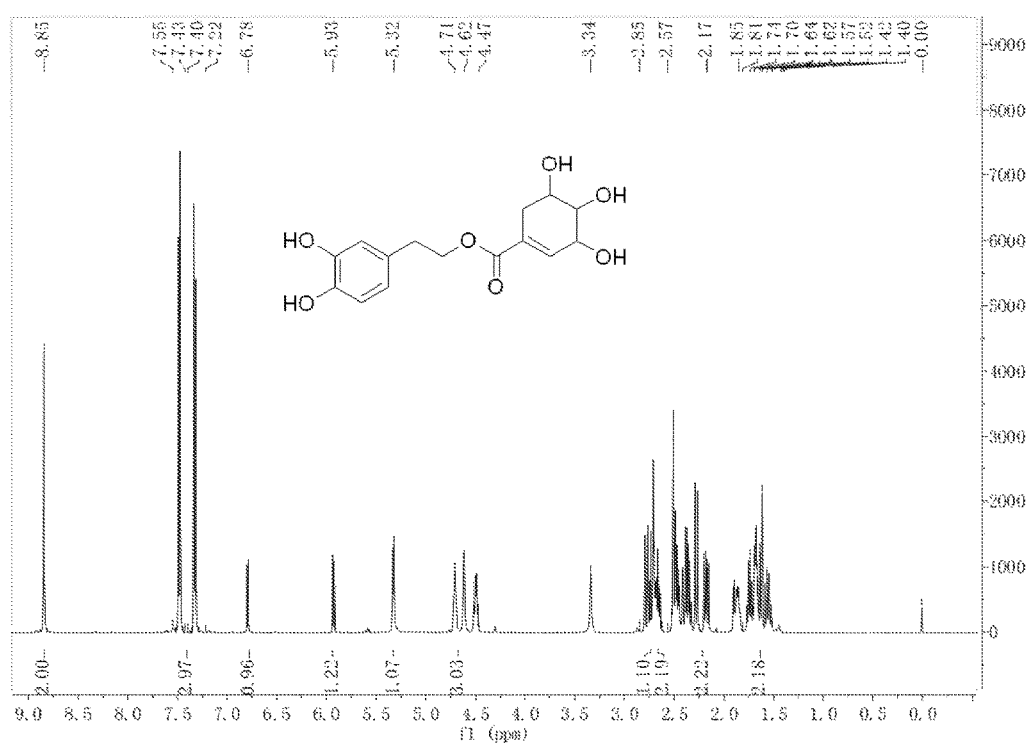
FIG. 1 is the $^1$HNMR spectrum of the hydroxytyrosol shikimic acid ester.
Figure 2:
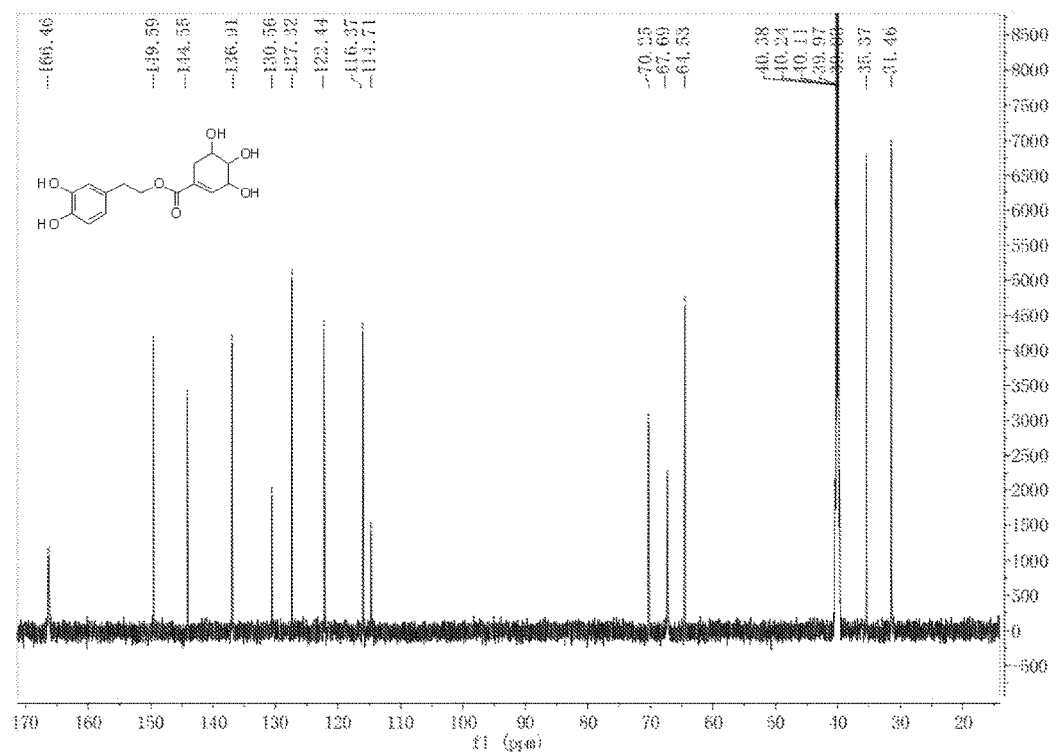
FIG. 2 is the $^{13}$CNMR spectrum of the hydroxytyrosol shikimic acid ester.

The $^1$H-NMR spectrum of the hydroxytyrosol shikimic acid ester is shown in FIG. 1, and the $^{13}$C-NMR spectrum is shown in FIG. 2.

Example 2

Preparation of the Hydroxytyrosol Shikimic Acid Ester 50 mg (0.32 mmol) of hydroxytyrosol and 51 mg (0.29 mmol) of shikimic acid were placed in a 100 mL reactor. 50 mL of THF (tetrahydrogenfuran) was added to dissolve hydroxytyrosol and shikimic acid. 55.6 mg (0.29 mmol) of EDC (1-Ethyl-3-(3-dimethylaminopropyl)carbodiimide) and 0.35 mg DMAP (4-Dimethylaminopyridine) were added to the reaction mixture under nitrogen atmosphere. The reaction mixture was heated at 50° C. under sonication for 3.5 hours. The mixture was then cooled to room temperature, and concentrated under reduced pressure. 50 mL ethyl acetate and 100 mL water were then added to the mixture, and the organic phase was collected and concentrated to give a crude product. The crude product was purified by flash chromatography to obtain 58.8 mg of target product, a yield of 76.5%.

Example 3

Preparation of the Hydroxytyrosol Shikimic Acid Ester 50 mg (0.32 mmol) of hydroxytyrosol and 36.6 mg (0.21 mmol) of shikimic acid were placed in a 100 mL reactor. 50 mL of acetonitrile was added to dissolve hydroxytyrosol and shikimic acid. 0.26 mg DMAP (4-Dimethylaminopyridine) and concentrated sulfuric acid were added to the reaction mixture under nitrogen atmosphere. The reaction mixture was heated at 50° C. under sonication for 4 hours. The mixture was then cooled to room temperature, and concentrated under reduced pressure. 50 mL ethyl acetate and 100 mL water were then added to the mixture, and the organic phase was collected and concentrated to give a crude product. The crude product was purified by flash chromatography to obtain 40.0 mg of target product, a yield of 61.4%.

Example 4

Preparation of the Hydroxytyrosol Shikimic Acid Ester 50 mg (0.32 mmol) of hydroxytyrosol and 47 mg (0.27 mmol) of shikimic acid were placed in a 100 mL reactor. 50 mL of DMF (Dimethylformamide) was added to dissolve hydroxytyrosol and shikimic acid. 0.33 mg DMAP (4-Dimethylaminopyridine) and concentrated sulfuric acid were added to the reaction mixture under nitrogen atmosphere. The reaction mixture was heated at 45° C. under sonication for 3 hours. The mixture was then cooled to room temperature, and concentrated under reduced pressure. 50 mL ethyl acetate and 100 mL water were then added to the mixture, and the organic phase was collected and concentrated to give a crude product. The crude product was purified by flash chromatography to obtain 61.3 mg of target product, a yield of 73.2%.

Example 5

Measurement of Thrombus Resolution Rate in Mice

Experimental materials: Clean-grade Kunming mice, weighing 20-28 g each, half male and half female; urokinase (Shanghai Maclean Biotechnology Co., Ltd.)

Experimental methods: 40 healthy Kunming mice were randomly divided into 5 groups according to their body weight, 8 in each group, half male and half female. One group of mice was selected as blank control. 1 mL of blood was taken from each mouse of the blank control group. After the blood was solidified, the formed blood clot (thrombus) was rinse with physiological saline for 30 minutes, and dried and weighed. The average weight of blood clot was calculated as W. Other groups of mice were treated with the same method. The blood clots were rinsed, and placed in cryotubes. 2 mL solutions of urokinase (positive control group), a low dose of hydroxytyrosol shikimic acid ester (experiment group 1), a medium dose of hydroxytyrosol shikimic acid ester (experimental group 2), and a high dose of hydroxytyrosol shikimic acid ester (experimental group 3) were added to the blood clots. For the blank control group, an equal volume of physiological saline was added to the blood clot. After incubating for 6 hours in a 37° C. incubator, the clots were taken out and rinsed with physiological saline for 30 min. After drying and weighing, the average weight of the blood clot was recorded as G, and the resolution rate of the blood clot was calculated according to the following formula.

Thrombus Resolution Rate (%)=[(W−G)/W]×100%

The resolution rates are shown in Table 1.

TABLE 1

Effect on Thrombus Resolution Rate in Mice

| Groups | Nos. of mice before and after tests | Concentration of test compounds | Resolution/% |
|---|---|---|---|
| Blank Control | 8/8 | / | 2.84 ± 0.35 |
| Positive Control | 8/8 | 0.5 U/mL | 12.38 ± 0.27*** |
| Experimental Group 1 | 8/8 | 2.5 mg/mL | 6.33 ± 0.19* |
| Experimental Group 2 | 8/8 | 5 mg/mL | 7.04 ± 0.41* |
| Experimental Group 3 | 8/8 | 10 mg/mL | 8.93 ± 0.45** |

*indicates a significant difference compared to the blank control group. Specifically, *($P < 0.05$), ($P < 0.01$), *($P < 0.001$).

As shown in Table 1, compared with the blank control group, the hydroxytyrosol shikimic acid ester experimental groups have obvious blood clot resolution (thrombolytic) effect, and as the concentration (dosage) increases, the resolution rate increases in a dose-dependent manner. This result indicates that, similar to the positive control, urokinase, hydroxytyrosol shikimic acid ester has a significant thrombolytic effect, and can be used as a cardiovascular drug.

Example 6

Measurement of thromboxane B2 (TXB2), 6-keto prostaglandin F1a (6-Ke-PGF1a) and prostaglandin E2 (PGE2) in rat plasma by enzyme-linked immunosorbent assay Experimental materials: clean grade SD rats, body weight 150-250 g, male; TXB2 radioimmunoassay kit, 6-Ke-PGF1a radioimmunoassay kit, PGE2 radioimmunoassay kit, Shanghai Bairui Biotechnology Co., Ltd.

Experimental methods: 32 rats were randomly divided into 4 groups, 8 rats in each group. After 2 days of normal feeding, blood was taken from the jugular vein of each rat, and the plasma was separated and frozen at −20° C. On the next day, rats in the experimental groups were intragastrically administered with low doses of hydroxytyrosol shikimic acid ester (experimental group 1), medium dose of hydroxytyrosol shikimic acid ester (experimental group 2) and high-dose hydroxytyrosol shikimic acid ester (experimental group 3) at a dose of 1 mL/100 g. Rats in the control group were intragastrically administered with the same amount of normal saline. After 20 days, blood was taken from the jugular vein of each rat, anticoagulated, and the plasma was separated and frozen at −20° C. The contents of plasma TXB2, 6-Ke-PGF1A and PGE2 in each group of rats were determined according to TXB2, 6-Ke-PGF1a and PGE2 kit methods. The experimental results are shown in Table 2.

TABLE 2

Effects on TXB2, PGE2, and 6-Ke-PGF1a Levels in Rat Plasma

| Groups | Nos. of rats before and after tests | Dosage (mg/Kg · d) | TXB2 (Pg/mL) | PGE2 (Pg/mL) | 6-Ke-PGF1a (Pg/mL) |
|---|---|---|---|---|---|
| Blank control | 8/8 | / | 5.66 ± 0.18 | 27.54 ± 0.14 | 62.42 ± 0.45 |
| Experimental 1 | 8/8 | 25 | 4.93 ± 0.12 | 26.18 ± 0.21 | 76.46 ± 0.17 |
| Experimental 2 | 8/8 | 50 | 4.38 ± 0.22 | 24.22 ± 0.14 | 85.40 ± 0.32* |
| Experimental 3 | 8/8 | 250 | 3.12 ± 0.14* | 20.87 ± 0.19* | 81.36 ± 0.28 |

*indicates a significant difference compared to the blank control group. Specifically, *($P < 0.05$).

As shown in Table 2, compared with the blank control group, the contents of TXB2 and PGE2 in the hydroxytyrosol shikimic acid ester experimental groups were reduced in a dose-dependent manner. The contents of Ke-PGF1a in the hydroxytyrosol shikimic acid ester experimental groups were increased, but there was no obvious dose-dependent relationship. The experimental results were statistically significant. TXB2 and 6-k-PGF1a are stable metabolites of thromboxane A2 (TXA2) and prostacyclin (PGI2), respectively. The increase of TXA2/PGI2 levels will cause platelet aggregation, thrombosis, and promote atherosclerosis and coronary heart disease. The results showed that the action of hydroxytyrosol shikimic acid ester resulted in a decrease in the contents of TXB2 and PGE2, and an increase in the content of 6-Ke-PGF1a, thereby maintaining the balance between thromboxane A2 (TXA2) and prostacyclin (PGI2) and promoting vasodilation and inhibiting thrombosis.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound having the following formula I:

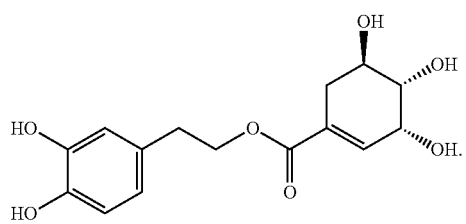

2. A method of preparing the compound of claim 1, comprising:
reacting the compound of formula II with the compound of formula III to obtain the compound of formula I:

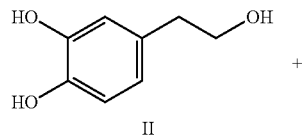

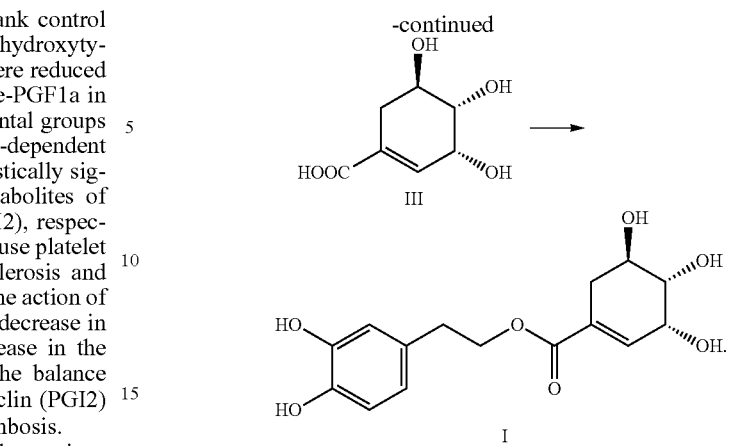

3. The method of claim 2, wherein the reaction of the compound of formula II with the compound of formula III comprises the following steps:
dissolving the compound of formula II and the compound of formula III in an organic solvent to form a reaction mixture under nitrogen atmosphere;
adding a catalyst and a dehydrating agent to the reaction mixture; and
heating the reaction mixture at 40-50° C. for 8-10 hours under sonication.

4. The method of claim 3, wherein the organic solvent is acetonitrile, THF, or DMF.

5. The method of claim 4, wherein the organic solvent is acetonitrile.

6. The method of claim 3, wherein the molar ratio of the compound of formula II and the compound of formula III is 1:1 to 1.5:1.

7. The method of claim 6, wherein the molar ratio of the compound of formula II and the compound of formula III is 1.2:1.

8. The method of claim 3, wherein the dehydrating agent is DCC, concentrated sulfuric acid, or EDC.

9. The method of claim 8, wherein the dehydrating agent is DCC.

10. The method of claim 3, wherein the catalyst is DMAP.

11. The method of claim 3, wherein the reaction mixture is heated at 45° C.

12. The method of claim 3, wherein the reaction mixture is heated for 4 hours.

* * * * *